(12) United States Patent
Beers

(10) Patent No.: US 11,464,684 B2
(45) Date of Patent: *Oct. 11, 2022

(54) SANITARY PROTECTIVE PANELS

(71) Applicant: Carly Jane Beers, Canyon Lake, TX (US)

(72) Inventor: Carly Jane Beers, Canyon Lake, TX (US)

(*) Notice: Subject to any disclaimer, the term of this patent is extended or adjusted under 35 U.S.C. 154(b) by 63 days.

This patent is subject to a terminal disclaimer.

(21) Appl. No.: 17/021,803

(22) Filed: Sep. 15, 2020

(65) Prior Publication Data

US 2021/0145659 A1 May 20, 2021

Related U.S. Application Data

(63) Continuation-in-part of application No. 16/686,501, filed on Nov. 18, 2019.

(51) Int. Cl.
*A61F 13/56* (2006.01)
*A61F 13/53* (2006.01)
*A61F 13/82* (2006.01)
*A61F 13/551* (2006.01)

(52) U.S. Cl.
CPC .......... *A61F 13/5605* (2013.01); *A61F 13/53* (2013.01); *A61F 13/551* (2013.01); *A61F 13/82* (2013.01); *A61F 2013/530029* (2013.01); *A61F 2013/53035* (2013.01); *A61F 2013/530036* (2013.01); *A61F 2013/530364* (2013.01)

(58) Field of Classification Search
None
See application file for complete search history.

(56) References Cited

U.S. PATENT DOCUMENTS

| 2,408,508 | A  | * | 10/1946 | Canavan | A61F 13/47245 |
| | | | | | 604/385.01 |
| 6,544,642 | B2 | * | 4/2003 | Cinelli | A61L 15/48 |
| | | | | | 428/343 |
| 7,927,322 | B2 | * | 4/2011 | Cohen | A61F 13/82 |
| | | | | | 604/385.03 |
| 9,820,892 | B2 | * | 11/2017 | Dennis | A61F 13/4704 |
| 2002/0115978 | A1 | * | 8/2002 | Cole | A61F 13/4756 |
| | | | | | 604/385.101 |
| 2006/0058760 | A1 | * | 3/2006 | Rosenfeld | A61F 13/472 |
| | | | | | 604/380 |

(Continued)

FOREIGN PATENT DOCUMENTS

WO   WO-2009019644 A2 * 2/2009   ......... A61F 13/5519

*Primary Examiner* — Arti Singh-Pandey
(74) *Attorney, Agent, or Firm* — Donald R. Boys; Central Coast Patent Agency LLC

(57) ABSTRACT

A sanitary protective napkin has a backing panel having an overall length, a width and a thickness, in a first shape having an outer periphery, an absorbent pad joined to the backing panel by a first adhesive on one side of the backing panel, the absorbent pad having a second shape, leaving a region of a common width around the outer periphery of the backing panel, and a second adhesive compatible with human skin applied to the region of common width around the periphery of the backing panel on the same side of the backing panel as the absorbent pad, enabling a user to apply the sanitary napkin with no undergarment or other device for anchoring the sanitary napkin.

10 Claims, 16 Drawing Sheets

(56) References Cited

U.S. PATENT DOCUMENTS

| | | | |
|---|---|---|---|
| 2009/0069771 A1* | 3/2009 | Yu | A61F 13/82 604/385.03 |
| 2009/0069780 A1* | 3/2009 | Plentovich | A61F 13/47227 604/385.05 |
| 2009/0171309 A1* | 7/2009 | VanDenBogart | A61F 15/001 604/385.03 |
| 2009/0182296 A1* | 7/2009 | Dennis | A61F 13/47209 604/385.03 |
| 2009/0198203 A1* | 8/2009 | Lira | A61F 13/56 604/385.03 |
| 2009/0204090 A1* | 8/2009 | Dennis | A61F 13/58 604/385.02 |
| 2009/0204092 A1* | 8/2009 | Loyd | A61F 13/622 604/385.03 |
| 2010/0121304 A1* | 5/2010 | Zhou | A61F 13/82 604/360 |
| 2010/0145294 A1* | 6/2010 | Song | G01N 33/558 604/361 |
| 2010/0152687 A1* | 6/2010 | Carlozzi | A61F 15/003 604/359 |
| 2010/0198177 A1* | 8/2010 | Yahiaoui | A61L 15/58 604/385.03 |
| 2013/0158494 A1* | 6/2013 | Ong | A61F 13/51 604/367 |
| 2013/0184665 A1* | 7/2013 | Kato | A61F 13/4704 604/374 |
| 2013/0345656 A1* | 12/2013 | Kato | A61F 13/4756 604/375 |
| 2014/0188065 A1* | 7/2014 | Defrancesco | A61F 13/4758 604/370 |
| 2014/0243779 A1* | 8/2014 | Kim | A61F 13/82 604/401 |

* cited by examiner

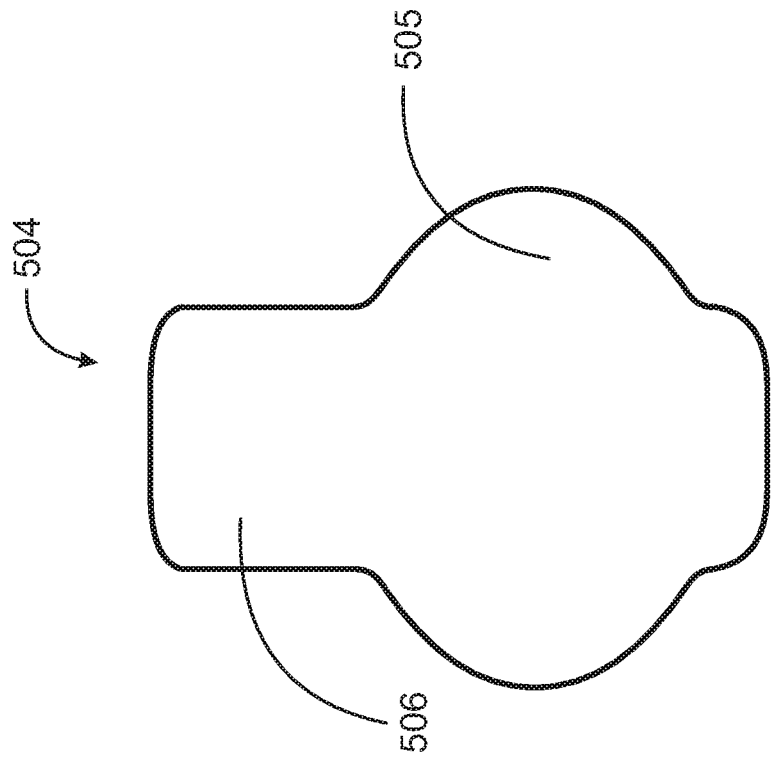
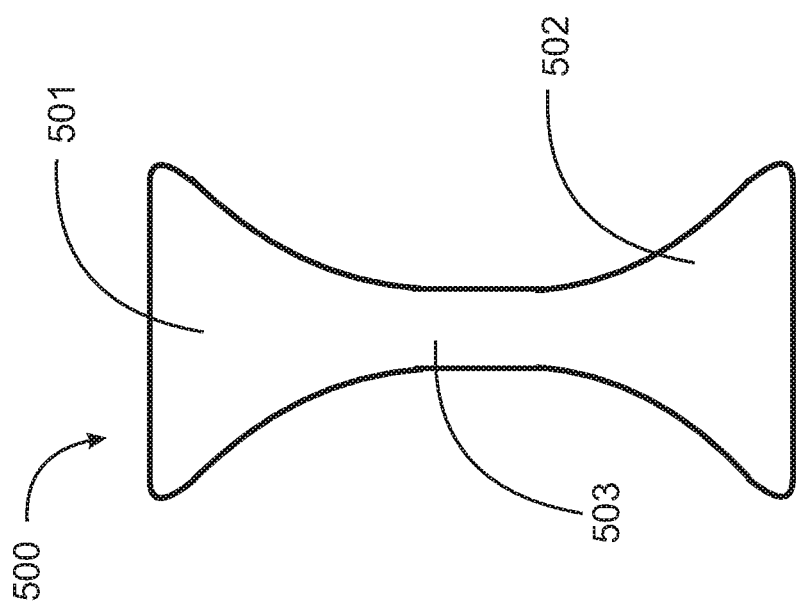
Fig. 5B
Fig. 5A

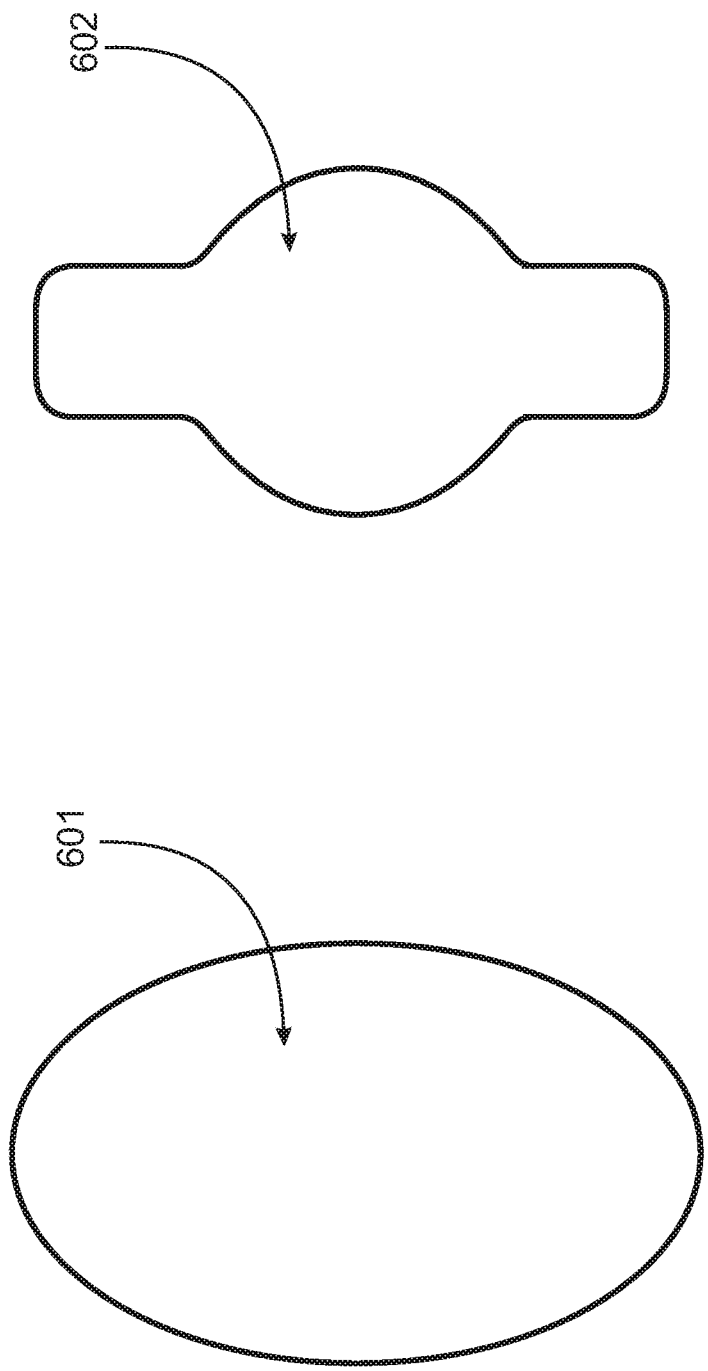

SANITARY PROTECTIVE PANELS

CROSS-REFERENCE TO RELATED DOCUMENTS

The present patent application is a continuation-in part (CIP) of co-pending non-provisional application Ser. No. 16/686,501, filed Nov. 18, 2019. Disclosure of prior application is incorporated herein in its entirety by reference.

BACKGROUND OF THE INVENTION

1. Field of the Invention

The present invention is in the technical area of sanitary protection during menstruation and pertains more particularly to provision of protective panels for as a sanitary pad for absorbing effluent during menstruation.

2. Description of Related Art

In retail transactions involving items of clothing it is well-known that customers of a retail establishment are motivated to try on articles of interest before agreeing to purchase, and most retail outlets have changing rooms with mirrors and clothes hangers where customers may take articles of clothing to try on same, and observe the fit and appearance in the selected clothing.

A very serious drawback in such retail outlets is simply that many, if not most customers, especially in enterprises offering such as lingerie, for example, are reluctant to try on articles that other customers may have already tried on. The problem being one of sanitation, and fear of contamination. It is well known, for example, that many diseases may be transmitted from bacteria or viruses that may be trapped on articles that have come into contact with genitalia.

It is known in the art that some retail establishments may have clothing for try-on that have protective panels sewn into the genital or underarm regions of the clothing. This may be seen as protecting the clothing but does nothing for protecting customers from cross-contamination.

Another unmet need in the art is a way for a woman to protect her clothing during menstruation while avoiding wearing undergarments.

What is clearly need is a sanitary protective napkin with absorbent material and adhesive around a periphery, such that the article may be applied to the needed region of the anatomy by the adhesive.

BRIEF SUMMARY OF THE INVENTION

In one embodiment of the invention a sanitary protective napkin is provided, comprising a backing panel having an overall length, a width and a thickness, in a first shape having an outer periphery, an absorbent pad joined to the backing panel by a first adhesive on one side of the backing panel, the absorbent pad having a second shape, leaving a region of a common width around the outer periphery of the backing panel, and a second adhesive compatible with human skin applied to the region of common width around the periphery of the backing panel on the same side of the backing panel as the absorbent pad, enabling a user to apply the sanitary napkin with no undergarment or other device for anchoring the sanitary napkin.

In one embodiment of the invention the first and the second adhesive are the same adhesive. Also, in one embodiment the first shape has a length, a common width along a portion of the length, and rounded ends. In one embodiment the absorbent material is cotton. And in one embodiment the absorbent material is one of or a combination of rayon, wood pulp, absorbent gel, cotton jersey, cotton flannel, hemp, micro-fiber, wool, or bamboo polyolefins.

In one embodiment the sanitary protective napkin further comprises a layer of soft fabric over the absorbent pad, the soft fabric adapted to pull liquid away from the skin into the absorbent pad. Also, in one embodiment the layer of soft fabric is 100% pure cotton. Also, in one embodiment the shape of the backing panel and the absorbent pad comprises a wide oval of a first width at an upper extremity, and a narrower second width at a lower extremity. In one embodiment the shape of the backing panel and the absorbent pad comprises a wide oval of a first width at an upper and at a lower extremity, and a middle portion of a more narrow width. And in one embodiment the sanitary protective napkin further comprises a paper envelope enclosing the sanitary protective napkin, the envelope comprising two layers with the sanitary protective napkin between the two layers, the two layers sealed around a periphery by an adhesive.

In another aspect of the invention a method for protecting a user's body and clothing during menstrual flow is provided, comprising tearing open a paper envelope enclosing a sanitary protective napkin comprising a backing panel having an overall length, a width and a thickness, in a first shape having an outer periphery, an absorbent pad joined to the backing panel by a first adhesive on one side of the backing panel, the absorbent pad having a second shape, leaving a region of a common width around the outer periphery of the backing panel, and a second adhesive compatible with human skin applied to the region of common width around the periphery of the backing panel on the same side of the backing panel as the absorbent pad, enabling a user to apply the sanitary napkin with no undergarment or other device for anchoring the sanitary napkin, removing the sanitary protective napkin from the opened envelope, and applying the sanitary protective napkin and securing the napkin to the user's skin by pressing the adhesive on the periphery of the sanitary protective napkin to the user's skin.

In one embodiment of the method the absorbent material is cotton. Also, in one embodiment the absorbent material is one of or a combination of rayon, wood pulp, absorbent gel, cotton jersey, cotton flannel, hemp, micro-fiber, wool, or bamboo polyolefins. In one embodiment the method further comprises providing a layer of soft fabric over the absorbent pad, the soft fabric adapted to pull liquid away from the skin into the absorbent pad. In one embodiment the layer of soft fabric is 100% pure cotton. In one embodiment the shape of the backing panel and the absorbent pad comprises a wide oval of a first width at an upper extremity, and a narrower second width at a lower extremity. And in one embodiment the shape of the backing panel and the absorbent pad comprises a wide oval of a first width at an upper and at a lower extremity, and a middle portion of a more narrow width.

BRIEF DESCRIPTION OF THE SEVERAL VIEWS OF THE DRAWINGS

FIGS. 5A and 5B depict alternative shapes of protective panels in another embodiment of the invention.

FIGS. 6A and 6B depict more alternative shapes of protective panels in another embodiment of the invention.

DETAILED DESCRIPTION OF THE INVENTION

Figure 1:
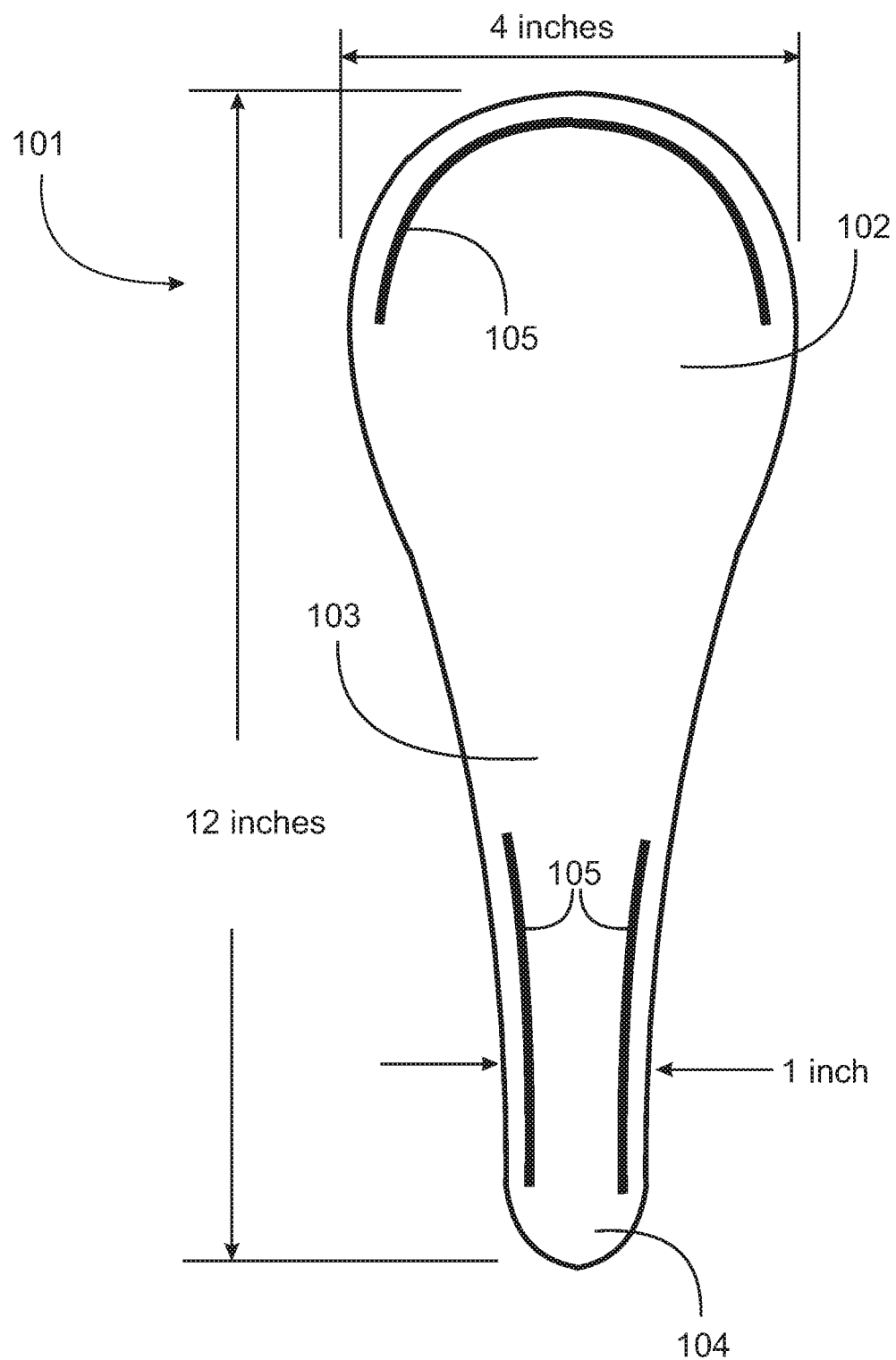
FIG. 1 is a plan view of a sanitary protective panel in an embodiment of the present invention.

FIG. 1 is a plan view of a sanitary protective panel 101 in an embodiment of the present invention. Panel 101 is a thin, shaped panel of polymer material, for example certain varieties of surgical tape. It is important that the material not be porous, or open cell, as an important purpose is to prevent penetration through the panel of bacteria, virus material, or liquids or semi-liquids, such as bodily fluids. In some embodiment the material may be hermetic. There are many plastic materials that may be suitable, and for some embodiments it is preferred that the panel material be opaque.

In this example panel 101 has an upper portion 102 in a shape of an oval with a widest portion at a centerline of the oval shape. In one embodiment the width may be about four inches but may vary in different embodiments from about three to about five inches. The panel has a lower section 103 tapering in width below upper section 102 from the width of four inches to a lower width of one inch at the lowermost rounded region Lines 105 of adhesive are placed on the panel in strategic peripheral places as shown. In some cases, the adhesive may as spots rather than lines. Spots may be oblong or oval.

Figure 2B:
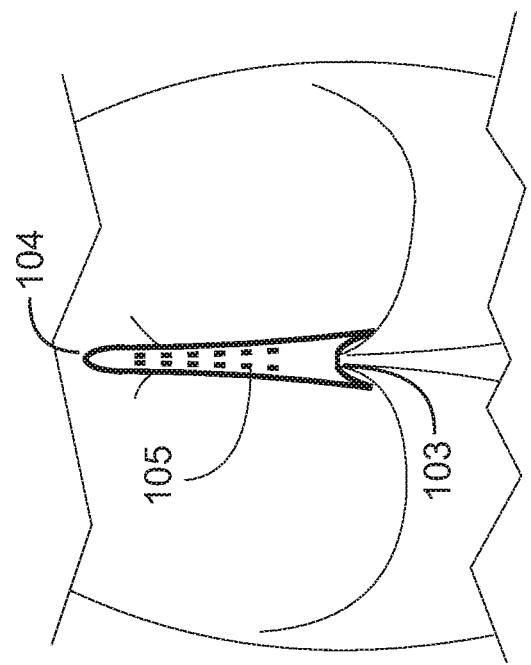
FIG. 2B is a rear elevation view of the midsection of the female person of FIG. 2A using a sanitary protective panel in an embodiment of the invention.
Figure 2A:
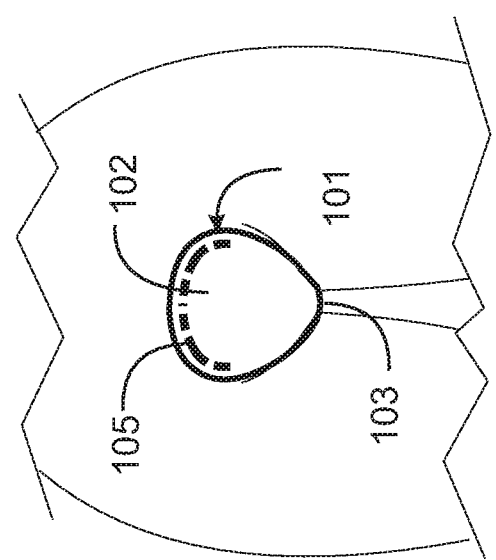
FIG. 2A is a front elevation view of a midsection of a female person using a sanitary protective panel in an embodiment of the invention.

FIGS. 2A and 2B illustrate a use of sanitary protective panel 101 in an embodiment of the invention. In FIG. 2A the essential shape of a female midsection is shown from a front view, outlined in relatively light lines, and in FIG. 2B the female midsection is illustrated from a back view, also in relatively light lines. Referring again to FIG. 2A, sanitary protective panel 101 is illustrated as mounted to the female form with the four-inch width of portion 102 positioned above the mons pubis (aka pubic mound), and the length of portion 102 descending to cover the front of the genital region, and to reach between the legs.

In this example panel 101 is joined to the female body by adhesive lines 105 around the periphery of section 102. When the user mounts panel 101, lower portion 103 will be suspended down the front of the user. This portion is passed between the legs and pulled up between the buttocks. In FIG. 2A this step has already been accomplished.

In back view FIG. 2B, the lower end 104 of panel 101 at one-inch wide is shown as mounted to the lower back of the female form above the buttocks, by one or more adhesive spots or lines of adhesive. Thus mounted to the female form, section 103 passing between the legs covers and protects both the vaginal opening and the anal opening, such that bacteria and fluids encountered in any activity may not enter these openings, and conversely, no fluid, material or such as bacteria from the wearers genital openings may be spread to any adjacent clothing or other person in any activity.

The inventor believes there are a variety of use cases for a sanitary protective panel according to embodiments of the present invention. One such is as pointed out in the background section above, that of retail clothing outlets where customers wish to try on articles of clothing but may hesitate because of the grossly unsanitary circumstance of putting on an article of clothing that another has worn next to the genitalia. Dispensing systems for sanitary protection panels according to the invention are described in enabling detail below, and a dispensing system may be provided in or near changing rooms in such retail outlets. Customers are enabled to take a sanitary protection panel from an enclosure, to don the panel, and to wear the panel while trying on different articles of clothing and are enabled to dispose of the panel in a sanitary manner after use. This practice protects both the customer and the business.

Another use case is in the practice of therapeutic massage, where clients may use such panels to avoid being completely exposed during massage sessions. The panels may also be fashioned for male use, wherein the upper panel may be somewhat wider or higher, and the male genitalia may be covered by the way the panel is positioned to the user's anatomy. Transgender individuals may find panels according to embodiments of the invention useful for hiding or taping back genital extremities.

There are many potential usages in medical practice, where patients may wish to cover the genitalia during an examination, for example. Such panels may be used when taking photos in medical examinations and diagnoses. The panels are also useful in any circumstance where a person needs to remove clothing to a near naked state but not completely naked. Sanitary disposal for medically related panels may have more emphasis than others. For example, a package that the panel comes in may also be used for disposal. The panels may be used for tanning beds so genitals are not exposed to ultraviolet (UV) radiation while tanning. In this use case the material may be UV resistant.

Persons may use such panels to protect the genital area from sand at the beach while still allowing for bikini exposure. The panels may also useful for such as mud runs, and any other activity where sealing the vaginal and anal openings from exposed elements is desired. The panels may be used by actors in shooting sex scenes where near full nudity may be required while still protecting and covering genitals of male and female from both physical and visual contact. Ladies that want to avoid panty line may use the panels instead of panties. With perhaps a shield lining, such as lead, panels according to the invention may protect pilots and scientists from harmful radiation.

Another use case derives from persons who want a sanitary alternative to conventional underwear. It is well known that excreta from the two genital openings, whether male or female, almost always stain and contaminate male and female panties and shorts. And it is not just the unsightly stains that are difficult for the laundry system to erase that is the problem. These stains are basically unsanitary, and bacteria and viruses can cross-contaminate other clothing and persons. Many persons may well choose to use a panel according to an embodiment of the invention to eliminate this unsightly and potentially dangerous circumstance. Such persons may well use one panel on dressing in the morning and carry one or panels during the day to use as needed. There may also be a sanitary disposal container for this use case.

Figure 3B:
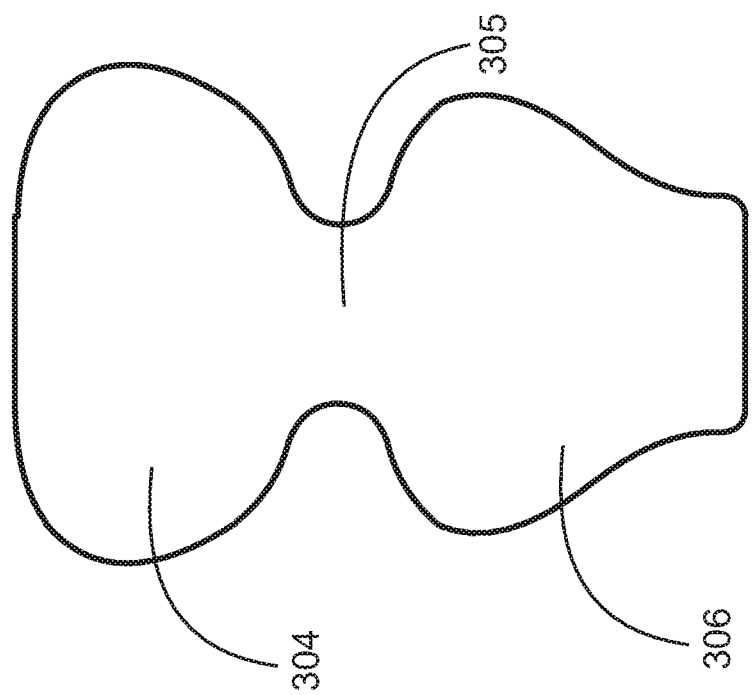
FIGS. 3A and 3B depict alternative shapes of protective panels in an embodiment of the invention.
Figure 3A:
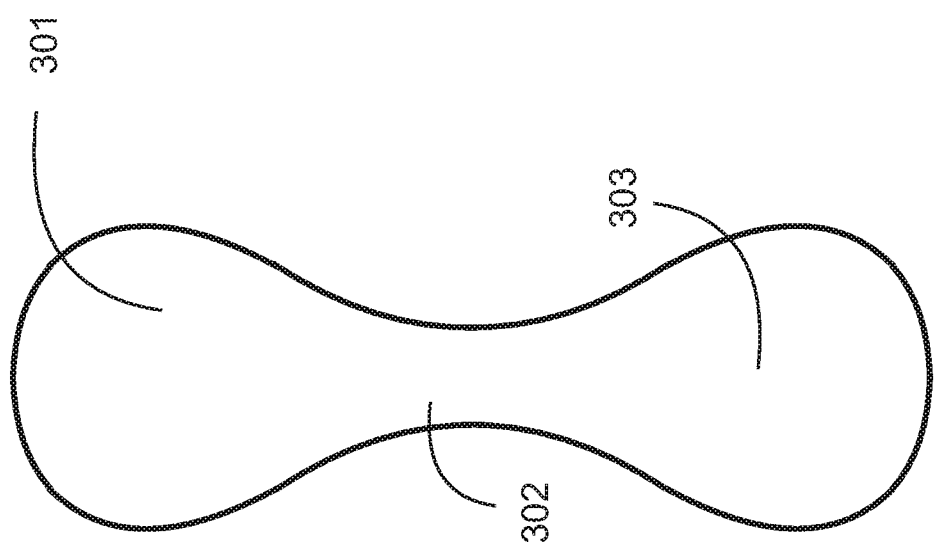

FIG. 3A is a plan view of a sanitary protective panel in an alternative embodiment of the present invention. In the panel of FIG. 3A there are two wider oval regions connected by a more narrow region. This panel may be used with either oval region at the front, and the other will make a wider shield behind the buttocks. FIG. 3B illustrates a panel intended for use by males, having wider regions.

Figure 4B:
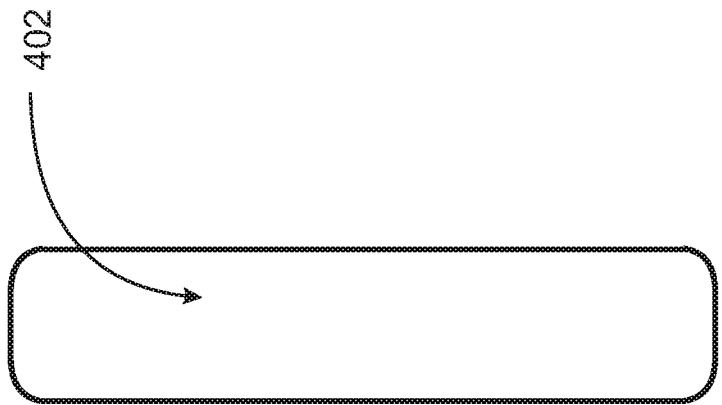
FIGS. 4A and 4B depict alternative shapes of protective panels in another embodiment of the invention.
Figure 4A:
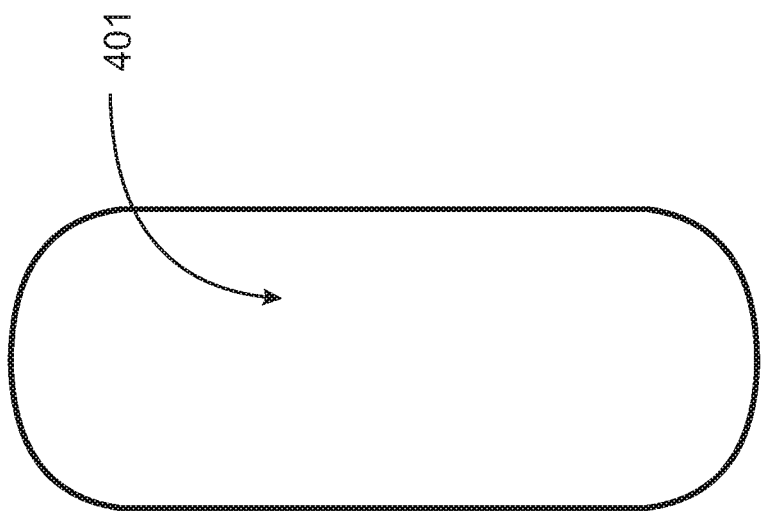

FIGS. 4A and 4B illustrate still more alternative shapes that are simpler in geometry. FIGS. 5A and 5B show more alternative shapes. FIGS. 6A and 6B illustrate shapes that might be used for underarm protection.

It has been described above that the panels in embodiments of the invention are sterile at the point in time that the user applies the panels to the user's body. This is because an important purpose is to prevent contamination for the user when, for example, trying on a garment that another person may have tried on, and that may therefore be contaminated with that other person's body fluids and bacteria, or even viruses.

Figure 7A:
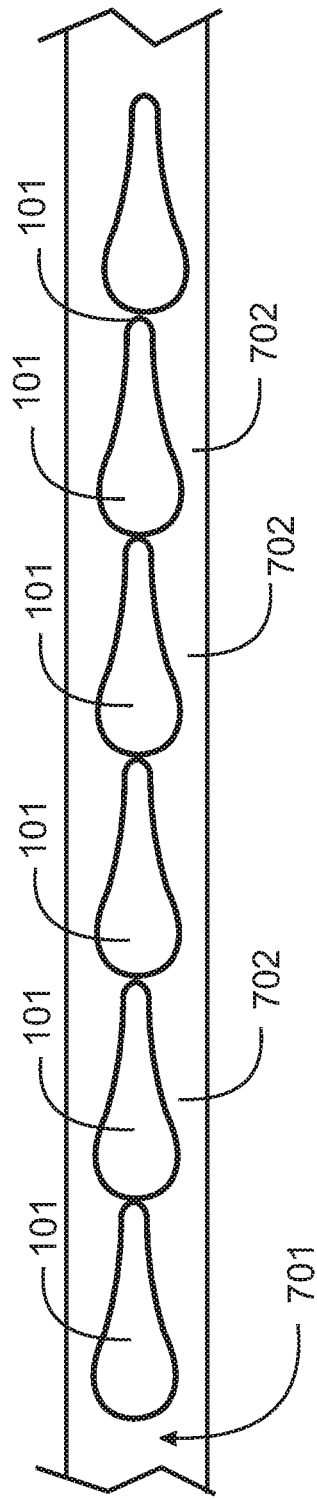
FIG. 7A shows a material strip with sanitary protective panels shown as sequential cut-outs.
Figure 7B:
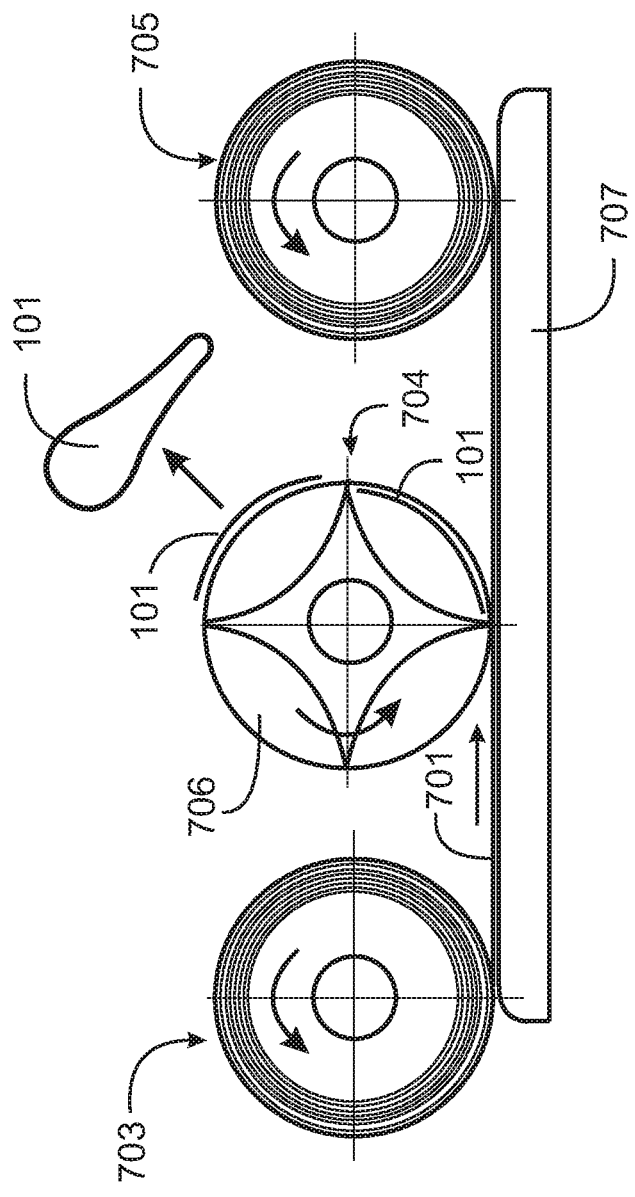
FIG. 7B is an elevation view of apparatus cutting sanitary protective panels from a continuous strip of material.

For it to be the case that the panels are always sterile at the point of use, the panels must be sterile at time of manufacture, and must be packaged and delivered in a way that the panels are sterile at the time that a user accesses a panel for personal use. FIGS. 7A and 7B are diagrams illustrating an exemplary process of manufacture.

FIG. 7A is a plan view of a strip of film 701 of a material and thickness suitable for a sanitary panel according to an embodiment of the present invention, preferably non-porous, of as thickness to be resistant to tearing or stretching. Film 701 is of a width such that cutting a panel 101 from film 701 will leave film on each side (702), enabling the film to be moved forward or backward as a whole before or after panels may be cut from the film. Panels 101 are shown end-to-end along a length of film 701.

FIG. 7B is an exemplary illustration depicting one way that panels 101 may be cut from film strip 701. In this example a substantial length of film 701 is provided on a roll 703, and film 701 is drawn along a backing panel 707 by a second roller 705, which rolls up used film after panels are cut from the film. Roller 705 may be powered and roller 703 may not be powered. A cutting roller 704 has, in this example, four cutting elements 706 that have cutting edges shaped to cut the shape of panels 101 from the advancing film. Roller 704 turns at just the necessary RPM to track along advancing film 701. As cutting elements 706 cut individual panels 201 from film 701, the panel just cut is retained on the cutting element as roller 704 turns and is removed at some point after the cutting process is complete. There are a variety of ways this may be accomplished, such as with suction cups on mechanical arms, and a variety of ways the cut panels may be collected and moved further through the process. An individual panel 101 is shown removed from a cutting element and turned arbitrarily to show the shape of the panel.

Figure 8A:
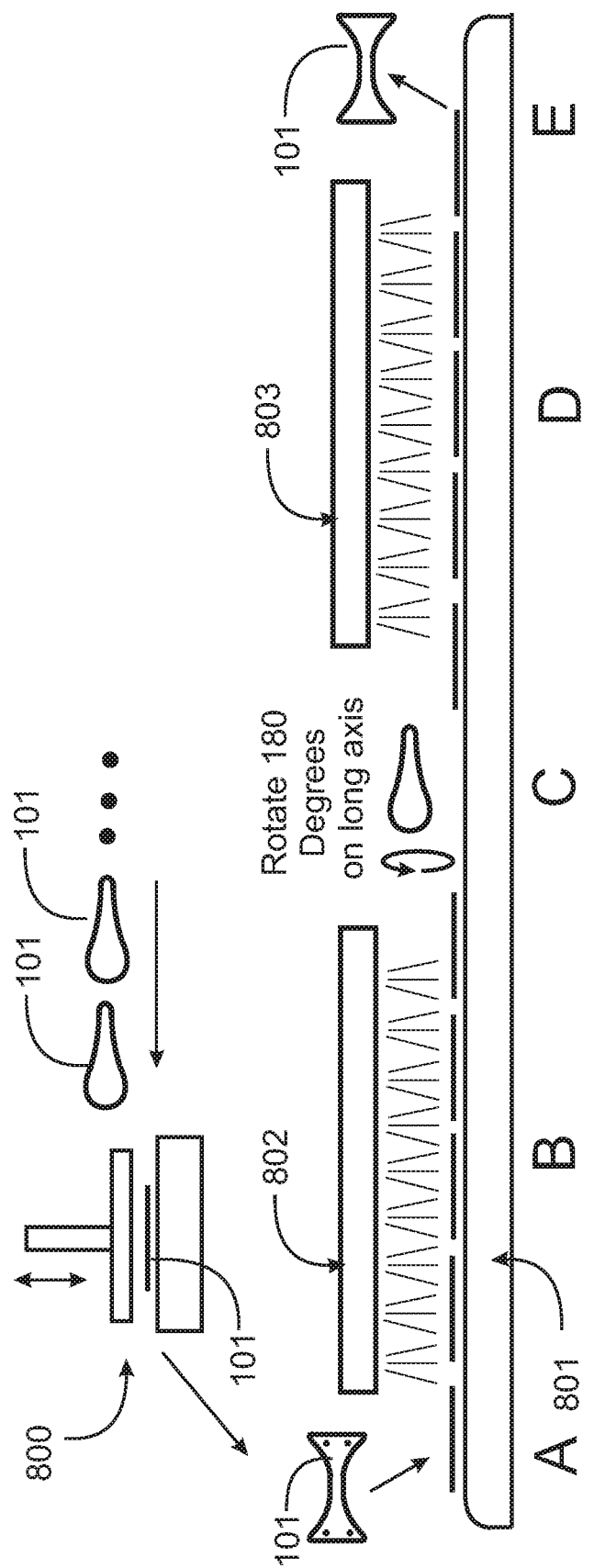
FIG. 8A shows apparatus applying adhesive to sanitary protective panels and sanitizing panels on both sides.

At the time of removal from the cutting elements the individual panels are formed, but not provided with adhesive, or cleaned or sanitized. FIG. 8A illustrates individual panels 101 being placed on an adhesive placement apparatus 800, where adhesive is added to each panel, after which panels with adhesive added are placed one at a time at a point A and translated along a path conveyance 801 through a region B where one side of each panel is cleaned and sanitized by a sanitizing apparatus 802. At point C along conveyance 801 panels 101 are rotated one hundred and eighty degrees around the length of the panel and placed back on conveyance 801. The panels then pass through a region D where the opposite side of each panel is cleaned and sanitized using a second sanitizing apparatus 803. At point E the panels are removed from the conveyance using sanitary apparatus and moved to another step in the process, keeping the panels sanitary in the process.

Figure 8B:
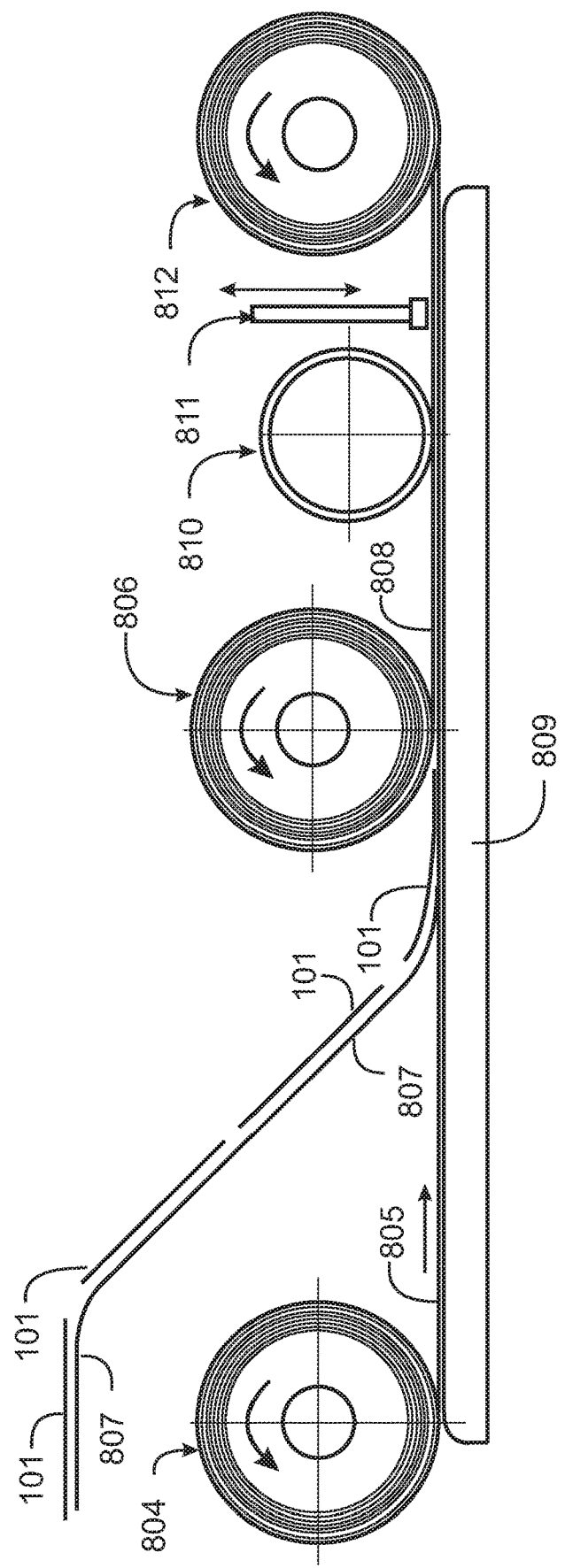
FIG. 8B is an elevation view of apparatus placing and capturing sanitary protective panels between two strips of film.

FIG. 8B is an elevation view of an exemplary apparatus packaging individual panels 101 between transparent sanitary plastic films, and heat sealing the films to enclose and protect the panels 101. In the example of FIG. 8B a roller 804 has a rolled length of transparent heat sealable film 805 of a width somewhat wider than the width of panels 101. There are several candidates for such film, such as, for example, polyethylene, polyolefin, polypropylene, and others. Film 805 is drawn along a backing panel 809 by a powered roller 812. Sanitary panels 101 are brought along a conveyance 807 and placed on film 805 as that film passes a point where the panels are placed. A roller 806 feeds a second transparent film 808 from a roller 806 over the top of panels 101 on film 805, sandwiching panels 101 between films 805 and 808. As the films advance further, with panels 101 captured between the films, a heat-sealing roller 810 seals opposite edges of films 805 and 808 together, and advancing further, a heat sealing bar 811 heat seals a strip 815 (see FIG. 8C) and also perforates a line in the center of the heat seal strip between each panel, enabling individual enclosed sanitary panels to be separated from the heat sealed strip. Dimension "s" (see FIG. 8C) represent the distance between panels 101 in the heat-sealed strip. The joined films enclosing panels 101 are rolled up finally on roller 812.

Figure 8C:
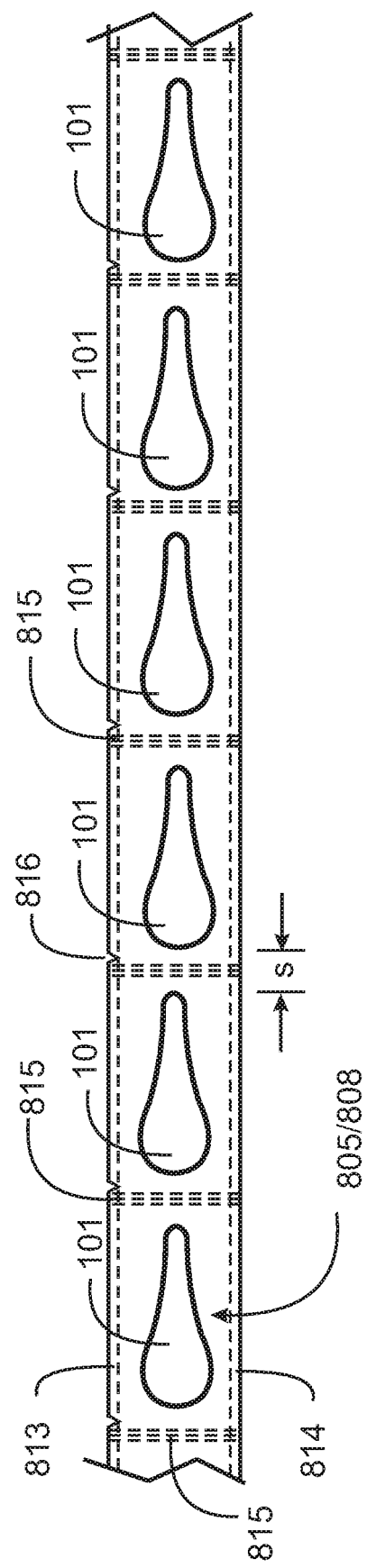
FIG. 8C is a plan view of sanitary protective panels captured between film strips with heat sealed edges and cross seals.

FIG. 8C illustrates the heat-sealed films 805 and 808 with panels 101 enclosed in individual pockets, formed by heat-sealed regions 813 and 814 along each side, and heat-sealed regions 815 between each panel 101. Regions 815 also have a perforated line for tearing off panels 701 from the strip.

Figure 9A:
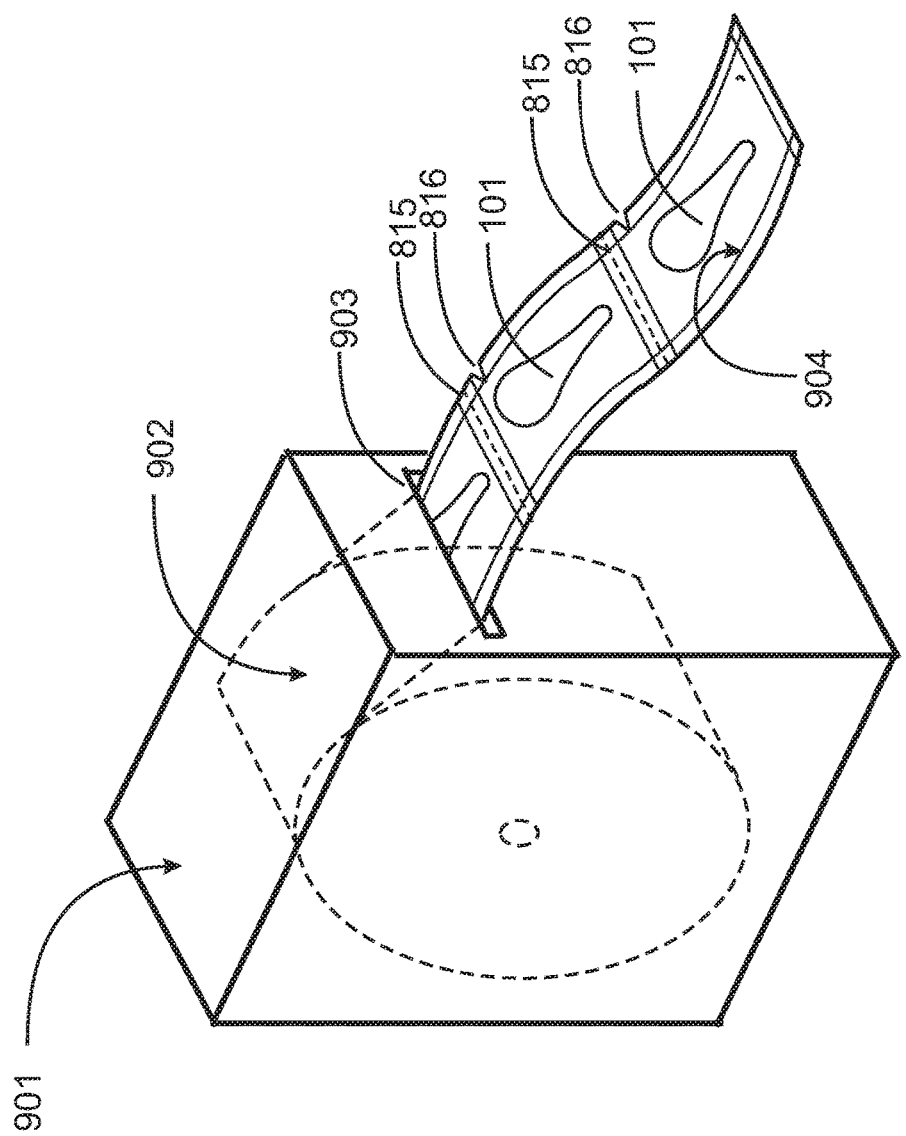
FIG. 9A is a perspective view of a dispenser providing packed sanitary protective panels in a strip for tearing off.

FIG. 9A illustrates a dispenser 901 enclosing a rolled inventory 902 of packaged panels 904, comprising individual panels 101 enclosed in film in a continuous roll enabled to feed packages 904 through a dispensing opening 903. Dispenser 901 may be mounted in a dressing room in a retail establishment, or in a central location in the retail establishment, and customers may tear off packages 904 one-by-one for personal use, along perf lines 815. The customer, having torn off one packaged panel, may tear open the sealed double film at a nick 816 on one side provided for the purpose (see also FIG. 8C for nick 816), to access a sanitary panel 101 with adhesive in the package.

Figure 9B:
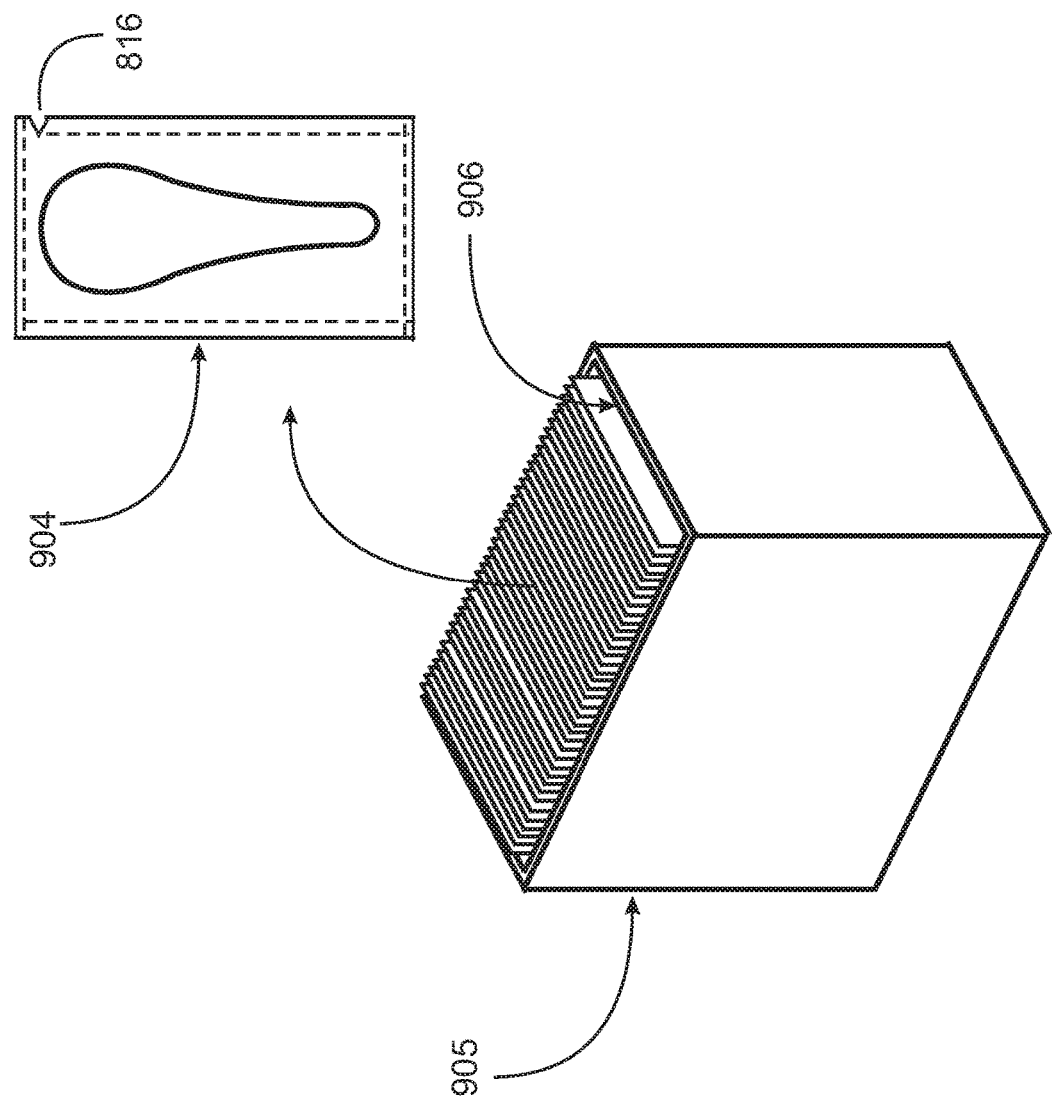
FIG. 9B is a perspective view of individual packages holding sanitary protective panels in a dispenser box for a user to take one-at-a-time.

FIG. 9B illustrates a dispenser box 905 having an open top 906, in which individual units 904, being each one an enclosed panel from a continuous strip, are displayed for use. The individual units may be automatically cut from the continuous strip and may be packed in dispenser boxes 905 as shown in FIG. 9B. A dispenser box of this sort may be placed in or near a changing room in a retail establishment, or individual units may be packed in units of such as two, five or ten, for example, to be sold to individual consumers, to be carried in a purse or a pocket for use as needed. The dispenser box has a removable top, not shown, that is closed when the dispenser is not in use.

FIG. 9B shows one package 904 having been removed from box 905, and shows nick 816, where a user may open the package to remove the sanitary panel 101 for personal use. In some embodiments a separate compartment may be provided with box 905 where the user may discard the panel 101 after use, and the package it came in as well. In other circumstances conventional trash receptacles may be provided for disposal of used panels and packages.

The adhesive with which a user applies a sanitary protective panel to his or her person in embodiments of the invention is a very important issue. There are adhesives for this purpose known in the art, and in most embodiments a suitable adhesive is selected from known adhesives. The nature of location and extent of the adhesive on a panel in embodiments of the invention is also an important issue. In some embodiments a panel according to an embodiment of the invention may be covered completely, or nearly so, on one side of the panel. A small region at one edge may be left sans adhesive so a user may grasp that small region to remove the panel after use. In some embodiments, adhesive may be applied to a panel in a continuous line around a periphery of a panel, and in other instances adhesive may be in spots as needed.

In another embodiment of the invention a unique maxi-pad is provided with absorbent material and adhesive for joining the maxi-pad to a user's skin in appropriate position to absorb effluent during time that the user is menstruating, in a manner that the user need not use undergarments or any other means of positioning and holding the maxi-pad in place.

Figure 10A:
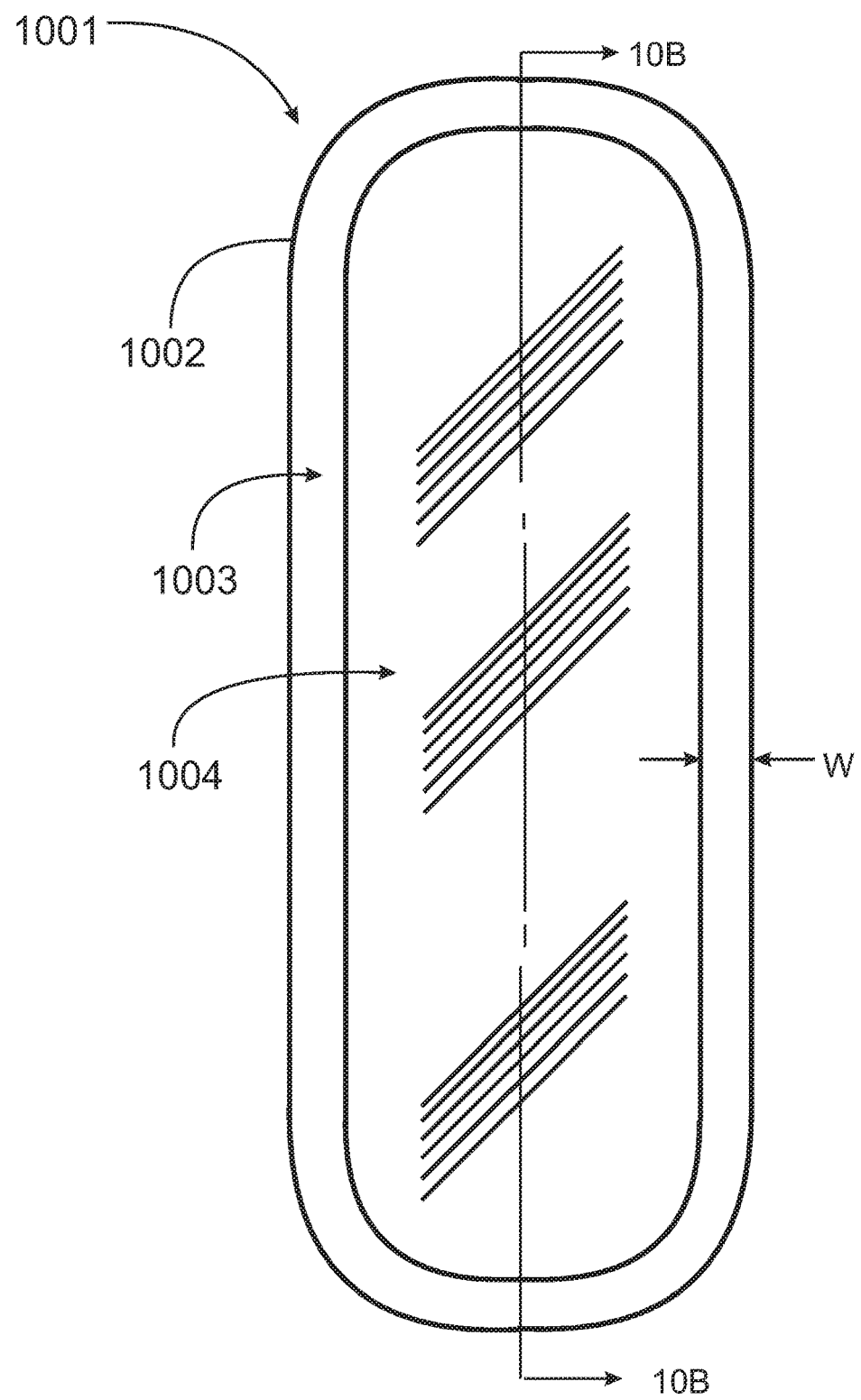
FIG. 10A is a plan view of a sanitary napkin with absorbent material in an embodiment of the invention.
Figure 10B:
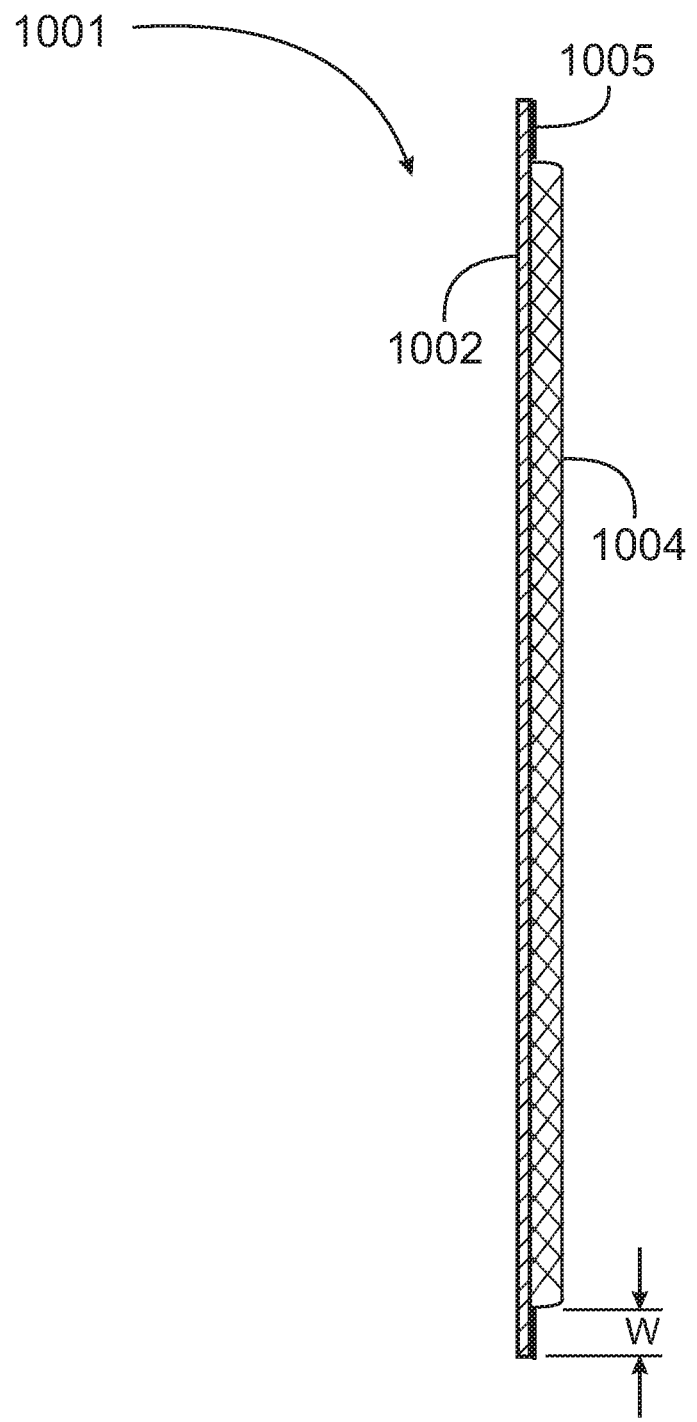
FIG. 10B is a side elevation section view of the sanitary napkin of FIG. 10A.

FIG. 10A is a plan view of a sanitary napkin 1001 with absorbent material 1004 in an embodiment of the invention. FIG. 10B is a side elevation section view of the sanitary napkin of FIG. 10A.

Sanitary napkin 1001 is based on a panel 1002 which may be a thin, shaped panel of fabric, paper or polymer film. It is important that the material not be porous, or open cell, as an important purpose is to prevent penetration through the panel of liquids or semi-liquids, such as bodily fluids. In some embodiment the material may be hermetic. There are many plastic materials that may be suitable, and for some embodiments it is preferred that the panel material be opaque.

In embodiments of the invention an absorbent pad 1004 is joined to a surface of panel 1002. Pad 1004 in one embodiment is cotton material but may also be any one of or a combination of, rayon, wood pulp, absorbent gel, cotton jersey, cotton flannel, hemp, micro-fiber, wool, or bamboo polyolefins. Absorbent pad 1004 may be joined to the surface of panel 1002 by an adhesive applied to one or both of the panel surface and one surface of the absorbent pad.

In one embodiment the absorbent layer may be covered with a soft fabric which pulls liquid away from the user's skin into the absorbent pad. This layer may be, for example, 100% pure cotton. The thickness of the absorbent layer may be different in different implementations. For example, there may be a version with a thickest pad for user's that typically exhibit a heavy menstrual flow, and other versions with less thickness for user's who do not exhibit a heavy menstrual flow.

Absorbent pad 1004 is of the shape of panel 102, but smaller in width and length to leave a peripheral region 1003 of a consistent width W all around the absorbent pad. A thin film of adhesive is applied to this peripheral region. This adhesive is ion the same surface of panel 1002 as is the absorbent pad. This is an adhesive with which a user applies a sanitary protective panel to her person in embodiments of the invention. There are adhesives compatible with human skin known in the art, and in most embodiments a suitable adhesive is selected from known adhesives.

An important feature of the invention is that the absorbent pad and the adhesive around the periphery on the same side of panel 1002 enables a user to apply the sanitary pad of the invention to her person by the adhesive around the periphery of the absorbent pad, and there is no need for any under-clothing or other device for placing or anchoring the sanitary napkin in an embodiment of the invention.

FIG. 10B, the section taken along line 10B-10B of FIG. 10A, shows absorbent pad 1004 joined to panel 1002, and the peripheral area with a thin coating 1005 of the adhesive that is compatible for sticking to the skin of the user. Width W may vary considerably in different embodiments, and in some embodiments adhesive 1005 may be applied across all of the surface of panel 1002, and absorbent pad 1004 may then be applied to panel 1002, leaving peripheral region 1003 covered with the same thin adhesive film.

Figure 11:
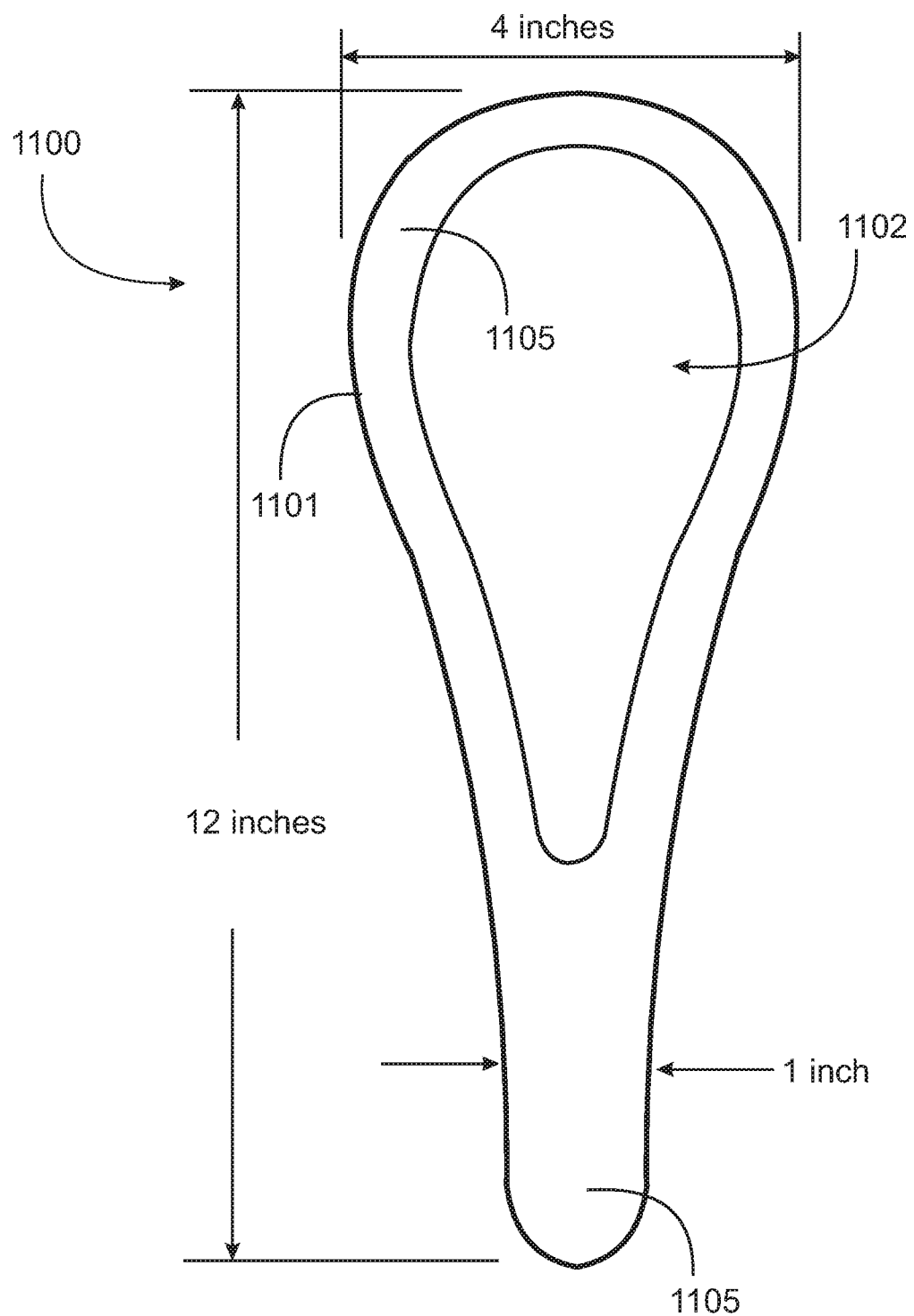
FIG. 11 is a plan view of a sanitary napkin with absorbent material in an embodiment of the invention, with a different shape than that of FIG. 10A.

FIG. 11 is a plan view of a sanitary napkin 1100 with an absorbent pad 1102 in an embodiment of the invention, with a different shape than that of FIG. 10A. Backing panel 1101 has a region 1105 around a periphery of the panel outside the shape of absorbent pad 1102. As described above, the absorbent pad my be applied using one adhesive, and a different adhesive may be applied to the outer region to join to the user's skin, or the same adhesive may be used for both purposes. The cross section in this case is much the same as shown in FIG. 10B. Further, the descriptions above for details and features of the embodiment described with reference to FIG. 10A apply as well to the pad with the shape as shown in FIG. 11. It is essentially the shape of the panel and pad that differs.

Figure 12:
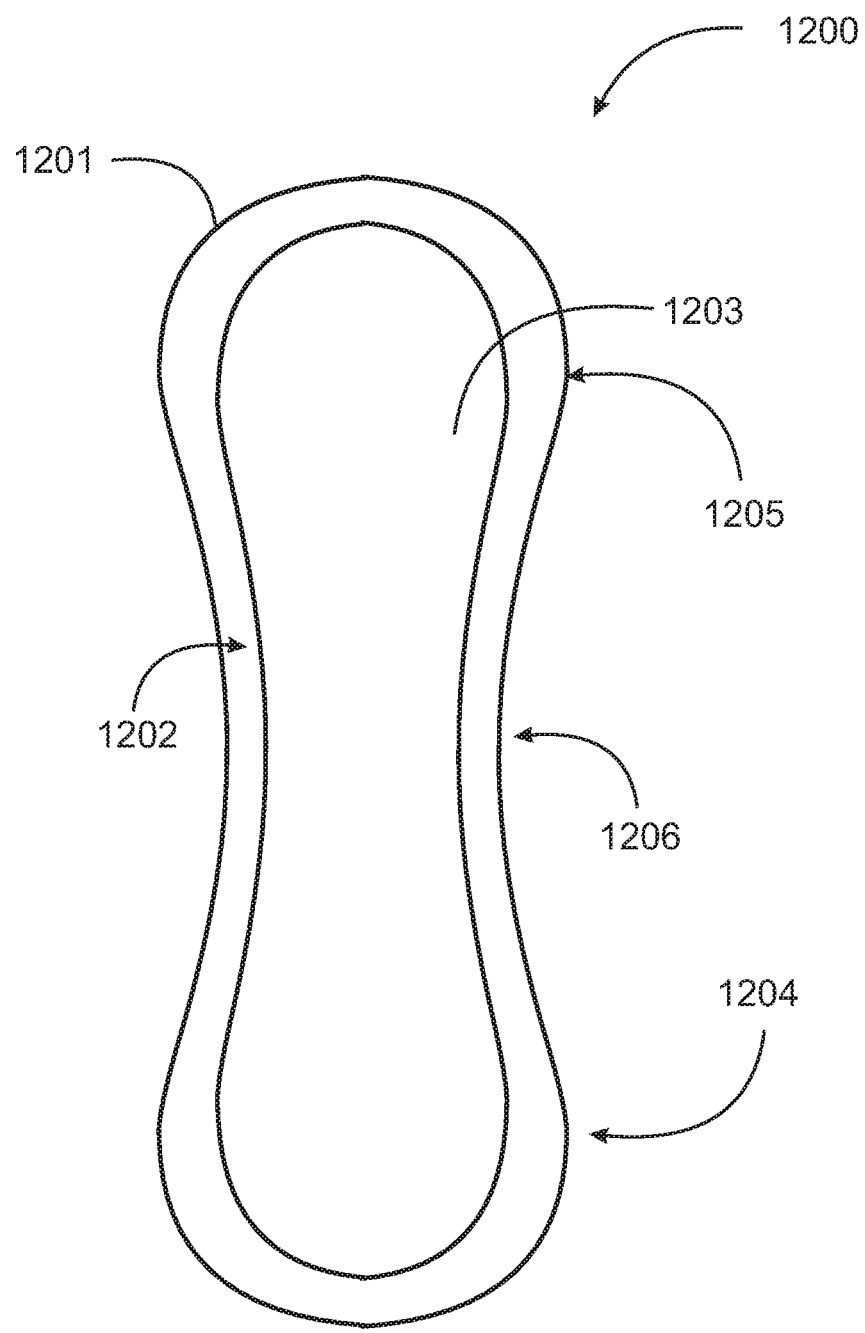
FIG. 12 is a plan view of a sanitary napkin with absorbent material in an embodiment of the invention, with a different shape than that of FIG. 10A or FIG. 11.

FIG. 12 is a plan view of a sanitary napkin 1200 with a panel 1201 and absorbent material 1203 in another embodiment of the invention, with a different shape than that of FIG. 10A or FIG. 11. In this example panel 1201 has a shape like an hourglass, with wider regions 1204 and 1205 joined by a narrow region 1206. The vertical cross section in this case is essentially the same as shown in FIG. 10B. As described above, absorbent pad 1203 may be joined to panel 1201 by a separate adhesive, or by a common adhesive over the entire surface of panel 1202, leaving peripheral region 1202 with a thin layer of the same adhesive for joining to the user's skin. Alternatively, different adhesives may be used for the absorbent pad and the peripheral region. Further, the descriptions above for details and features of the embodiment described with reference to FIG. 10A apply as well to the pad with the shape as shown in FIG. 11.

In some embodiments of the invention the sanitary protective napkin is enclosed in an envelope, the envelope comprising two layers with the sanitary protective napkin between the two layers, the two layers sealed around a periphery by an adhesive. The envelop may be paper and sealed such that an edge may be torn open to access the sanitary protective napkin.

A person of skill in the art will understand that the embodiments described above are entirely exemplary, and not limiting to the scope of the invention. There may be many changes made in the embodiments shown above within the scope of the invention.

The invention claimed is:

1. A sanitary protective napkin, comprising:
a backing panel having an overall length, an overall width, a garment-facing surface, a body-facing surface and a thickness, the backing panel having a first size and an outer periphery in a specific shape;
an absorbent pad of a cohesive fabric having an outer periphery in the specific shape of the outer periphery of the backing panel, the absorbent pad having an overall width and length less than the overall width and length of the backing panel, a front surface and a back surface, and a thickness substantially greater than the thickness of the backing panel, the absorbent pad joined to the body-facing surface of the backing panel over the back surface of the absorbent pad by a first adhesive, leaving a region of the body-facing surface of the backing panel exposed between the outer periphery of the absorbent pad and the outer periphery of the backing panel; and
a second adhesive compatible with human skin applied to the region between the outer periphery of the backing panel on the body-facing surface, and the outer periphery of the absorbent pad, enabling a user to apply the sanitary napkin to the user's body with the absorbent pad completely enclosed by the backing panel.

2. The sanitary protective napkin of claim 1, wherein the first and the second adhesive are the same adhesive.

3. The sanitary protective napkin of claim 1, wherein the first shape has a length, a common width along a portion of the length, and rounded ends.

4. The sanitary protective napkin of claim 1, wherein the absorbent material is cotton.

5. The sanitary protective napkin of claim 1, wherein the absorbent material is one of or a combination of rayon, wood pulp, absorbent gel, cotton jersey, cotton flannel, hemp, micro-fiber, wool, or bamboo polyolefins.

6. The sanitary protective napkin of claim 1, further comprising a wicking layer of soft fabric over the absorbent pad, the wicking layer adapted to pull liquid away from the skin into the absorbent pad.

7. The sanitary protective napkin of claim 6, wherein the layer of soft fabric is 100% pure cotton.

8. The sanitary protective napkin of claim 1, wherein the shape of the backing panel and the absorbent pad comprises a wide oval of a first width at an upper extremity, and a narrower second width at a lower extremity.

9. The sanitary protective napkin of claim 1, wherein the shape of the backing panel and the absorbent pad comprises a wide oval of a first width at an upper and at a lower extremity, and a middle portion of a more narrow width.

10. The sanitary protective napkin of claim 1, further comprising a paper envelope enclosing the sanitary protective napkin, the envelope comprising two layers with the sanitary protective napkin between the two layers, the two layers sealed around a periphery by an adhesive.

* * * * *